US012807698B2

(12) United States Patent
Avigdor et al.

(10) Patent No.: US 12,807,698 B2
(45) Date of Patent: Nov. 24, 2026

(54) TREATING SKIN IRRITATION FROM APPLICATION OF AN ALTERNATING ELECTRIC FIELD

(71) Applicant: Novocure GmbH, Root (CH)

(72) Inventors: Lilach Avigdor, Haifa (IL); Tali Voloshin-Sela, Haifa (IL); Uri Weinberg, Haifa (IL)

(73) Assignee: Novocure GmbH, Baar (CH)

( * ) Notice: Subject to any disclaimer, the term of this patent is extended or adjusted under 35 U.S.C. 154(b) by 503 days.

(21) Appl. No.: 18/371,625

(22) Filed: Sep. 22, 2023

(65) Prior Publication Data

US 2024/0101661 A1 Mar. 28, 2024

Related U.S. Application Data

(60) Provisional application No. 63/409,581, filed on Sep. 23, 2022.

(51) Int. Cl.
*A61K 31/351* (2006.01)
*A61K 31/427* (2006.01)
*A61N 1/40* (2006.01)
*C07K 16/24* (2006.01)

(52) U.S. Cl.
CPC .......... *C07K 16/244* (2013.01); *A61K 31/351* (2013.01); *A61K 31/427* (2013.01); *A61N 1/40* (2013.01)

(58) Field of Classification Search
CPC .................................................... A61K 31/351
See application file for complete search history.

(56) References Cited

U.S. PATENT DOCUMENTS

| | | | | |
|---|---|---|---|---|
| 7,565,205 | B2 * | 7/2009 | Palti | A61N 1/40 607/76 |
| 2017/0152273 | A1 * | 6/2017 | Merchant | A61K 47/06 |
| 2019/0091350 | A1 * | 3/2019 | Peyman | A61K 49/227 |

FOREIGN PATENT DOCUMENTS

| | | | |
|---|---|---|---|
| WO | 2005/115535 | A2 | 12/2005 |

OTHER PUBLICATIONS

Pastor-Fernandez et al, Cells 2020, 9(9), 2044 (Year: 2020).*
Chen et al (Asia-Pacific Journal of Oncology Nursing, vol. 9, Iss 8, Aug. 2022). (Year: 2022).*
Bianchi et al., "Editorial: Role of the IL-23/IL-17 Pathway in Chronic Immune-Mediated Inflammatory Diseases: Mechanisms and Targeted Therapies," Frontiers in Immunology, vol. 12, Article 770275, Sep. 2021, 4 pages.
Bugaut et al., "Major Role of the IL 17/23 Axis in Psoriasis Supports the Development of New Targeted Therapies," Frontiers in Immunology, vol. 12, Article 621956, Feb. 2021, 8 pages.
Vecellio et al., "The IL-17/IL-23 Axis and Its Genetic Contribution to Psoriatic Arthritis," Frontiers in Immunology, vol. 11, Article 596086, Jan. 2021, 10 pages.
Isono et al., "Inhibiting RORγt/Th17 axis for autoimmune disorders," Drug Discovery Today, vol. 19, No. 8, Aug. 2014, 7 pages.
(Continued)

*Primary Examiner* — Benjamin J Packard
(74) *Attorney, Agent, or Firm* — McCarter & English, LLP; Michael A. Sartori

(57) ABSTRACT

A method for treating a subject, the method comprises delivering an interleukin 23 (IL-23) inhibitor to the subject and applying an alternating electric field to the subject at a frequency between approximately 50 kHz and approximately 10,000 kHz.

25 Claims, 7 Drawing Sheets

(56) References Cited

OTHER PUBLICATIONS

Liu et al., "The IL-23/IL-17 Pathway in Inflammatory Skin Diseases: From Bench to Bedside," Frontiers In Immunology, vol. 11, Article 594735, Nov. 2020, 13 pages.
Wawrzycki et al., "Interleukin-22 and its Correlation with Disease Activity in Plaque Psoriasis," Archivum Immunologiae Therapiae Experimentalis, (2019) 67:103-108.
Wolk et al., "IL-22 Increases the Innate Immunity of Tissues," Immunity, vol. 21, 241-254, Aug. 2004.
Zheng et al., "Interleukin-22, a potent target for treatment of non-autoimmune diseases," Human Vaccines & Immunotherapeutics, 2018, vol. 14, No. 12, 2811-2819.
Chiricozzi et al., "Increased expression of interleukin-17 pathway genes in nonlesional skin of moderate-to-sever psoriasis vulgaris," British Journal of Dermatology, (2016), 174, pp. 136-145.
Katie Hobbins, "Tailor Treatment to Achieve Best Outcomes," DermatologyTimes.com, Nov. 2021, 1 page.
Michalak-Stoma et al., "IL-17A in the Psoriatic Patients' Serum and Plaque Scales as Potential Marker of the Diseases Severity and Obesity", Mediators of Inflammation, vol. 2020, Article ID 7420823, 9 pages.
Brian J. Nickoloff, "Cracking the cytokine code in psoriasis," Nature Medicine, vol. 13, No. 3, Mar. 2007, 3 pages.
Study of Safety and Efficacy of Topical GSK2981278 Ointment in Plaque Psoriasis, ClinicalTrials.gov, May 15, 2017, 11 pages.
Markota, et al., "Targeting interleukin-22 for cancer therapy," Human Vaccines & Immunotherapeutics, 2018, vol. 14, No. 8, 2012-2015.
Chen et al., "Management of dermatologic adverse events associated with tumor treating fields in patients with glioblastoma multiforme: A 27-case series," Asia-Pacific Journal of Oncology Nursing 9 (2022), 6 pages.
Lacouture et al., "Prevention and Management of Dermatologic Adverse Events Associated With Tumor Treating Fields in Patients with Glioblastoma," Frontiers in Oncology, vol. 10, Article 1045, Jul. 2020, 13 pages.

* cited by examiner

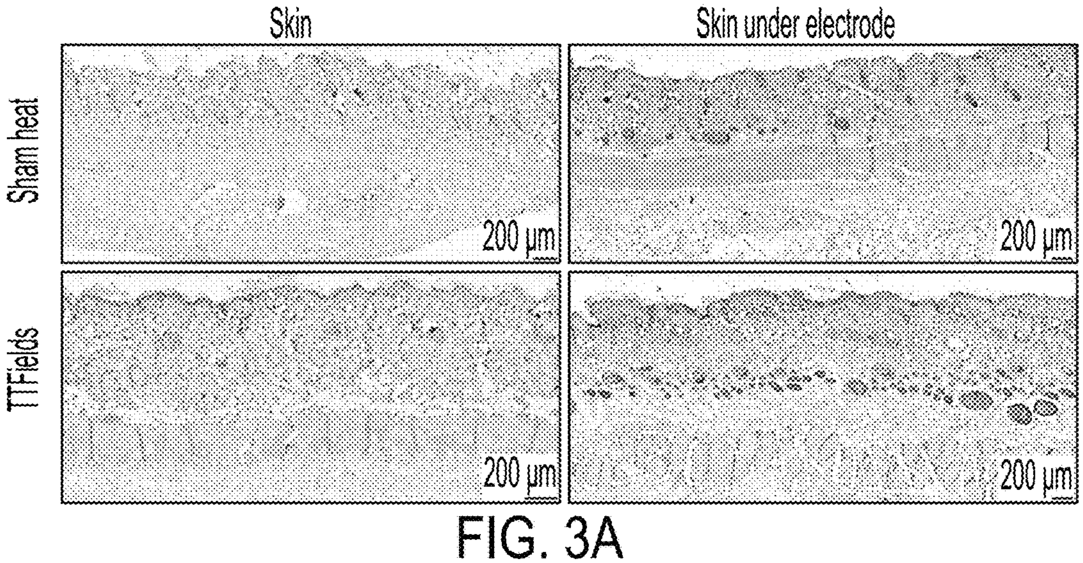
FIG. 3A
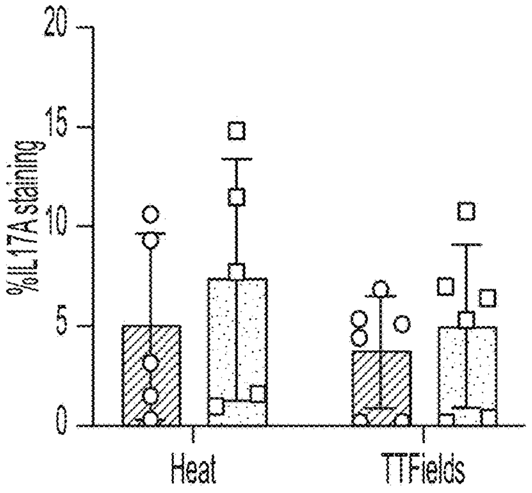
FIG. 3B
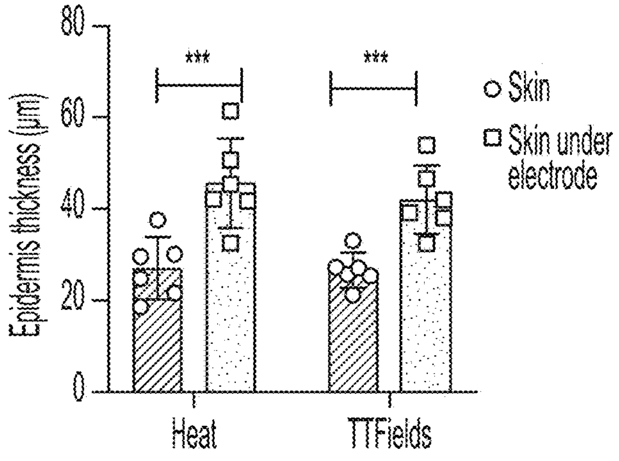
FIG. 3C
| Elisa results | Fold change in IL23 | Fold change in IL17 |
|---|---|---|
| No treat | 1.00 | 1 |
| Heat | 1.01 | 1.37 |
| TTFields | 1.19 | 1.34 |
FIG. 3D

TREATING SKIN IRRITATION FROM APPLICATION OF AN ALTERNATING ELECTRIC FIELD

CROSS-REFERENCE TO RELATED APPLICATIONS

This application claims priority to U.S. Provisional Application No. 63/409,581, filed on Sep. 23, 2022, the entire contents of which are incorporated by reference herein in their entirety.

BACKGROUND

Tumor treating fields (TTFields) are low-intensity alternating electric fields within the intermediate frequency range, which may be used to treat tumors as described in U.S. Pat. No. 7,565,205. TTFields are induced non-invasively into a region of interest by transducers placed directly on a patient's body and applying AC voltages between the transducers. AC voltage is applied between a first pair of transducers for a first interval of time to generate an electric field with field lines generally running in the front-back direction. Then, AC voltage is applied at the same frequency between a second pair of transducers for a second interval of time to generate an electric field with field lines generally running in the right-left direction. The system then repeats this two-step sequence throughout the treatment.

BRIEF DESCRIPTION OF THE DRAWINGS

FIGS. 3A-3D depict the effects of alternating electric fields on the release of IL-17A and the formation of epidermis thickness.

DESCRIPTION OF EMBODIMENTS

The inventors have discovered techniques for treating skin irritation following alternating electric field treatment of a subject. The present disclosure relates to systems and methods for treating skin irritation caused by the Tumor Treating Fields (TTFields) treatment. For example, the present disclosure provides methods and systems for reducing and/or preventing the release of the alternating electric field-induced-inflammatory cytokines/proteins. As used herein, the terms "prevent," "preventing," or "prevention" refer to reducing the probability of developing a disorder or condition in a subject who does not have but is at risk of or susceptible to developing a disorder or condition. The prevention can be complete (i.e., no detectable symptoms) or partial so that fewer symptoms are observed than would likely occur absent treatment.

Figure 1:
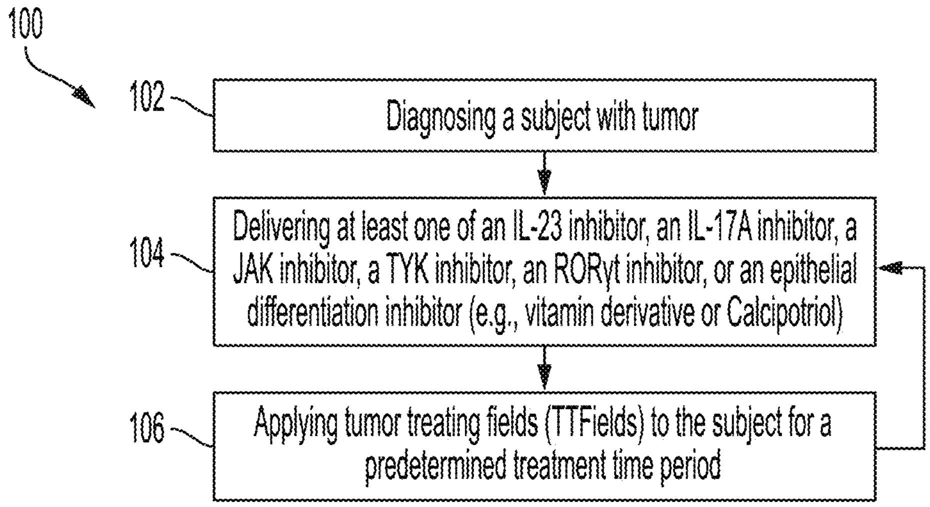
FIG. 1 depicts example approaches for treating a subject in accordance with exemplary embodiments of the present disclosure.

FIG. 1 depicts an example method 100 of treating skin irritation caused by the application of the alternating electric field (e.g., TTFields) in accordance with exemplary embodiments of the present disclosure. At step 102, a subject with a certain disorder can be diagnosed. In one example, the disorder can include tumors, cancers, or other disorders that can be treated by the alternating electric field. As used herein, "subject," "subject in need thereof," "patient," and "patient in need thereof" are used interchangeably and refer to an animal or living organism (human or nonhuman) suffering from or prone to a disease or condition that can be treated by applying the alternating electric field. Non-limiting examples of subjects include humans, other mammals, bovines, rats, mice, dogs, monkeys, goats, sheep, cows, deer, and other non-mammalian animals. In certain embodiments, the subject is human.

The disclosed alternating electric field (e.g., TTFields) is a physical modality therapy that can be used for the treatment of various symptoms and indications (e.g., cancer, tumor, hormonal disorder, etc.). When treating a subject using alternating electric fields, a certain level of amplitude and/or frequency of the alternating electric field can be required for effective treatment. As used herein, an "effective treatment" is the treatment sufficient to affect a desired biological effect, such as beneficial results, including clinical results. As such, an "effective treatment" depends upon the context in which it is being applied. An amount and/or condition of the alternating electric field for an effective treatment can vary according to factors known in the art, such as the disease state, age, sex, and weight of the individual being treated.

The application of the alternating electric field (e.g., TTFields) with certain frequency ranges and amplitude ranges can cause skin irritation by promoting the release of inflammatory cytokines and/or proteins. For example, the application of the alternating electric field can stimulate interleukin 17 (IL-17)/interleukin 23 (IL-23) pathways and promote the release of inflammatory cytokines/proteins.

IL-17 can be produced by T helper (Th) 17, gamma delta (γδ) T lymphocytes, Mucosal-Associated Invariant T (MAIT) cells, or Innate Lymphoid Cells (ILC) 3 in response to inflammatory stimuli. Th17 phenotype can be stabilized by IL-23, which can be synthesized by macrophages and dendritic cells in response to Toll-Like Receptors and C-type Lectin Receptors stimulation. In addition to Th17, other innate subsets, such as unconventional T cells, can be a source of IL17 in psoriasis. Plasmacytoid dendritic cells (pDCs) then can secrete type I interferon and tumor-necrosis alpha (TNFα), which activate classical dendritic cells (cDCs). These cDCs can produce IL-12 and IL-23 and skew the differentiation of naïve T cells into T helper (Th) 1, Th17 and Th22 cells. Th17 cell survival and expansion depend on IL-23. Interleukin 23 receptor (IL-23R) can be induced in Th17 by IL-6 signaling through Janus kinases (JAK) JAK1, JAK2, tyrosine kinase 2 (TYK2), STAT3, and RAR-related orphan receptor gamma t (RORγt). The participation of IL-23 is important in the differentiation of IL-17-expressing phenotypes via activating the transcription factor retinoid-related orphan receptor-γt (ROR-γt) and signal transducer and activator of transcription 3 (STAT3). The key complex, which consists of IL-17A/A, IL-17A/F, or IL-17F/F cytokine and IL-17RA or IL-17RC, is the start hallmark of IL-17 signaling transduction.

IL-23 can also promote epidermal hyperplasia activating the proliferation of keratinocytes. By acting synergistically with IL-17, IL-23 can promote the recruitment of neutrophils and the infiltration of IL-22 and IL-17 producing-cells into the lesioned skin. IL-17 and IL-22 both promote keratinocyte proliferation and the recruitment of macrophages and neutrophils. They can also decrease the expression of adhesion molecules (i.e., selectins and integrins), thus favoring the disruption of the skin barrier. The recruitment of pathogenic IL-23/IL-17-producing CD4+ T-cells has been demonstrated to be higher in the joints, while the IL-17/IL-22 producing CD4+ T-cells are strongly detected in the skin and in the circulation. The action of IL-22 can be mainly restricted to epithelial cells. Dysregulated IL-22 production can be associated with certain inflammatory skin diseases such as atopic dermatitis and psoriasis.

IL-22 also induces phosphorylation of Jak1 and Tyk2. Moreover, activation of the MAP kinase pathways and serine phosphorylation of STATS can be required for maximum IL-22-induced transactivation of STAT-responsive promoters in these cells. IL-22 can collaborate with other soluble factors and cells together, forming inflammatory circuits that otherwise exist as constitutive or inducible pathways in normal skin and become pathologically amplificated in psoriasis.

T lymphocytes, specifically CD4+ T cells or T helper (Th) cells, can act as the primary sources of IL-22 production. A unidirectional flow of cytokine signaling can be seen in the case of IL-22, as immune cells act as the main source of secretion for IL-22, while its main targets include non-hematopoietic epithelial cells. For this reason, IL-22 can be considered as an essential factor of immune-epithelial crosstalk. Th1 and Th17 cells can be major producers of IL-22. IL-22 production by CD4+ cells can be mainly mediated by cytokines like IL-23, IL-21, IL-12, IL-1β, IL-7, IL-6, TNF-α (Tumor Necrosis Factor) and some other molecules like Notch, RORγt and aryl hydrocarbon receptor ligand like FICZ [6-formylindolo[3,2-b] carbazole.

The application of the alternating electric field (e.g., TTFields) can cause skin irritation by promoting the release of inflammatory cytokines and/or proteins.

At step 104 of FIG. 1, an inhibitor for treating or preventing skin irritation and/or epidermal turnover and proliferation can be delivered to a subject. In one example, the inhibitor can include at least one of an IL-23 inhibitor, an IL-17A inhibitor, a RAR-related orphan receptor gamma (RORγt) inhibitor, an interleukin 17F (IL-17F) inhibitor, an interleukin 17 receptor α (IL-17RA) inhibitor, an interleukin 12 receptor β1 (IL-12Rβ1 inhibitor), an interleukin 23 receptor (IL-23R) inhibitor, an IL-22 inhibitor, a Janus kinase (JAK) inhibitor, a non-receptor tyrosine-protein kinase (TYK2) inhibitor, or an inhibitor of epithelial differentiation (e.g., a vitamin D derivative such as calcipotriol).

In certain embodiments, the inhibitor can be delivered to the subject through various techniques. In one example, the inhibitor can be administered to the subject orally. For example, at least one of an IL-23 inhibitor, an IL-17A inhibitor, a RAR-related orphan receptor gamma (RORγt) inhibitor, an interleukin 17F (IL-17F) inhibitor, an interleukin 17 receptor α (IL-17RA) inhibitor, an interleukin 12 receptor β1 (IL-12Rβ1 inhibitor), an interleukin 23 receptor (IL-23R) inhibitor, an IL-22 inhibitor, a Janus kinase (JAK) inhibitor, a non-receptor tyrosine-protein kinase (TYK2) inhibitor, or a vitamin D derivative can be formulated as tablets, pills, capsules, liquids, gels, syrups, slurries, suspensions and the like, for oral or nasal ingestion by a subject to be treated. In one example, the disclosed inhibitors can be administered to the subject parenterally. The terms "parenteral administration" and "administered parenterally," as used herein, refer to the administration other than enteral and topical administration, usually by injection, and include, without limitation, intravenous, intramuscular, intraarterial, intrathecal, intracapsular, intracardiac, intradermal, intraperitoneal, transtracheal, subcutaneous, subcuticular, intraarticular, subcapsular, subarachnoid, intraspinal, epidural and intrasternal injection and infusion. For example, and not by way of limitation, the disclosed inhibitor can be topically administered to a subject. In some examples of topical administration, the inhibitor can be formulated as an ointment, cream, hydrogel, nanoparticle, adhesive material or bioactive glue.

In one example, the IL-23 inhibitor can include at least one of guselkumab, risankizumab, or tildrakizumab. A dosage of the IL-23 inhibitor can range from approximately 5 mg to approximately 200 mg. In one example, at least a portion of the alternating electric field can be applied to a subject after at least a portion of the IL-23 inhibitor is delivered. In one example, at least a portion of the alternating electric field can be simultaneously applied with delivering at least a portion of the IL-23 inhibitor. For example, a portion of the IL-23 inhibitor can be delivered to the subject at least approximately 5, 10, 15, 20, or 30 minutes before the applying the alternating electric field to a subject. In one example, at least a portion of the alternating electric field can be applied to a subject before at least a portion of the IL-23 inhibitor is delivered. For example, a portion of the IL-23 inhibitor can be delivered to the subject at least approximately 1 minute after applying the alternating electric field to a subject. In one example, the IL-23 inhibitor can be delivered to a subject prior to the alternating electric field treatment or at least one day after starting the alternating electric field treatment (e.g., 3-4 days).

In one example, the IL-17A inhibitor can include at least one of secukinumab, ixekizumab, or brodalumab. In one example, the IL-17A inhibitor is a dual IL-17A and IL-17F inhibitor, such as bimekizumab. The dosage of the IL-17A inhibitor can range from approximately 45 mg to approximately 300 mg. In one example, at least a portion of the alternating electric field can be applied to a subject after at least a portion of the IL-17A inhibitor is delivered. In one example, at least a portion of the alternating electric field can be simultaneously applied with delivering at least a portion of the IL-17A inhibitor. For example, a portion of the IL-17A inhibitor can be delivered to the subject at least approximately 5, 10, 15, 20, or 30 minutes before the applying the alternating electric field to a subject. In one example, at least a portion of the alternating electric field can be applied to a subject before at least a portion of the IL-17A inhibitor is delivered. For example, a portion of the IL-17A inhibitor can be delivered to the subject at least approximately 1 minute after the applying the alternating electric field to a subject. In one example, the IL-17A inhibitor can be delivered to a subject prior to the alternating electric field treatment or at least one day after starting the alternating electric field treatment (e.g., 3-4 days).

In one example, the RORγt inhibitor can include at least one of JNJ-61803534, AZD0284, GSK2981278, ML209, or SR221. A dosage of the RORγt inhibitor can range from approximately 5 mg to approximately 600 mg once or twice daily. In one example, at least a portion of the alternating electric field can be applied to a subject after at least a portion of the RORγt inhibitor is delivered. In one example, at least a portion of the alternating electric field can be simultaneously applied with delivering at least a portion of the RORγt inhibitor. For example, a portion of the RORγt inhibitor can be delivered to the subject at least approximately 5, 10, 15, 20, or 30 minutes before the applying the alternating electric field to a subject. In one example, at least a portion of the alternating electric field can be applied to a subject before at least a portion of the RORγt inhibitor is delivered. For example, a portion of the RORγt inhibitor can be delivered to the subject at least approximately 1 minute after the applying the alternating electric field to a subject. In one example, the RORγt inhibitor can be delivered to a subject prior to the alternating electric field treatment or at least one day after starting the alternating electric field treatment (e.g., 3-4 days).

In one example, the IL-17F inhibitor can include at least one of the disclosed IL-17A inhibitors. For example, the IL-17F inhibitor can include at least one of secukinumab, ixekizumab, or brodalumab. In one example, the IL-17F inhibitor is a dual IL-17A and IL-17F inhibitor, such as bimekizumab. The dosage of the IL-17F inhibitor can range from approximately 45 mg to approximately 300 mg. In one example, at least a portion of the alternating electric field can be applied to a subject after at least a portion of the IL-17F inhibitor is delivered. In one example, at least a portion of the alternating electric field can be simultaneously applied with delivering at least a portion of the IL-17F inhibitor. For example, a portion of the IL-17F inhibitor can be delivered to the subject at least approximately 5, 10, 15, 20, or 30 minutes before the applying the alternating electric field to a subject. In one example, at least a portion of the alternating electric field can be applied to a subject before at least a portion of the IL-17F inhibitor is delivered. For example, a portion of the IL-17F inhibitor can be delivered to the subject at least approximately 1 minute after the applying the alternating electric field to a subject. In one example, the IL-17F inhibitor can be delivered to a subject prior to the alternating electric field treatment or at least one day after starting the alternating electric field treatment (e.g., 3-4 days).

In one example, the IL-12Rβ1 inhibitor can include at least one of Ustekinumab, (R)-Lisofyline, Apilimod mesylate, Apilimod, and Isomucronulatol. A dosage of the IL-12Rβ1 inhibitor can range from approximately 45 mg once a week to approximately 200 mg twice a week. In one example, at least a portion of the alternating electric field can be applied to a subject after at least a portion of the IL-12Rβ1 inhibitor is delivered. In one example, at least a portion of the alternating electric field can be simultaneously applied with delivering at least a portion of the IL-12Rβ1 inhibitor. For example, a portion of the IL-12Rβ1 inhibitor can be delivered to the subject at least approximately 5, 10, 15, 20, or 30 minutes before the applying the alternating electric field to a subject. In one example, at least a portion of the alternating electric field can be applied to a subject before at least a portion of the IL-12Rβ1 inhibitor is delivered. For example, a portion of the IL-12Rβ1 inhibitor can be delivered to the subject at least approximately 1 minute after the applying the alternating electric field to a subject.

In one example, the IL-17RA inhibitor can include at least one of Brodalumab, FM-202, or Anti-IL-12p40/IL-23p40 Human Abs. A dosage of the IL-17RA inhibitor can range from approximately 100 mg to approximately 700 mg. In one example, at least a portion of the alternating electric field can be applied to a subject after at least a portion of the IL-17RA inhibitor is delivered. In one example, at least a portion of the alternating electric field can be simultaneously applied with delivering at least a portion of the IL-17RA inhibitor. For example, a portion of the IL-17RA inhibitor can be delivered to the subject at least approximately 5, 10, 15, 20, or 30 minutes before the applying the alternating electric field to a subject. In one example, at least a portion of the alternating electric field can be applied to a subject before at least a portion of the IL-17RA inhibitor is delivered. For example, a portion of the IL-17RA inhibitor can be delivered to the subject at least approximately 1 minute after the applying the alternating electric field to a subject.

In one example, the IL-23R inhibitor can include at least one of Ustekinumab, Briakinumab, FM-202, FM-303, IL-23 Adnectin, ADC-1012, Anti-IL-12p40/IL-23p40 HumAbs, Anti-IL-23 HumAbs, Apilimod, LY-2525623, irikizumab (LY3074828), risankizumab (BI655066/ABBV066), brazikumab (MEDI2070, formerly AMG139), and guselkumab (CNTO1959). A dosage of the IL-23R inhibitor can range from approximately 18 mg to approximately 200 mg. In one example, at least a portion of the alternating electric field can be applied to a subject after at least a portion of the IL-23R inhibitor is delivered. In one example, at least a portion of the alternating electric field can be simultaneously applied with delivering at least a portion of the IL-23R inhibitor. For example, a portion of the IL-23R inhibitor can be delivered to the subject at least approximately 5, 10, 15, 20, or 30 minutes before the applying the alternating electric field to a subject. In one example, at least a portion of the alternating electric field can be applied to a subject before at least a portion of the IL-23R inhibitor is delivered. For example, a portion of the IL-23R inhibitor can be delivered to the subject at least approximately 1 minute after the applying the alternating electric field to a subject.

In one example, the IL-22 inhibitor can include at least one of Fezakinumab, an IL-22 binding protein. A dosage of the IL-22 inhibitor can range from approximately 100 mg to approximately 600 mg. In one example, at least a portion of the alternating electric field can be applied to a subject after at least a portion of the IL-22 inhibitor is delivered. In one example, at least a portion of the alternating electric field can be simultaneously applied with delivering at least a portion of the IL-22 inhibitor. For example, a portion of the IL-22 inhibitor can be delivered to the subject at least approximately 5, 10, 15, 20, or 30 minutes before the applying the alternating electric field to a subject. In one example, at least a portion of the alternating electric field can be applied to a subject before at least a portion of the IL-22 inhibitor is delivered. For example, a portion of the IL-22 inhibitor can be delivered to the subject at least approximately 1 minute after the applying the alternating electric field to a subject.

In one example, the JAK inhibitor can include at least one of Opzelura, Tofacitinib, AZD4604, Filgonitib, Ruxolitinib, NVP-BSK805, Cerdulatinib, Phenylpyropene C, Delphinidine, GLPG0634, Momelotinib, Baricitinib, Decernotinib, SJ10542, XL019, Pyridone 6, SHR0302, Itacitinib, Peficitinib, Deuruxolitinib, PF-06263276, SAR-20347, WP1066, Ilginatinib, FM-381, BMS-911543, TG101209, Fedratinib, Cucurbitacin I, FM-479, Golidocitinib, BD750, Solcitinib, MS-1020, Oclactinib, CHZ868, Brepocitinib, Baricitinib, SC99, WHI-P97, AZD-1480, Reticiline, LFM-A13, TCS21311, G5-7, SD-1008, Abrocotinib, Upadactinib, AZ-3, FLL32, GDC-4379, GDC-43, NSC33994, Ilunocitinib, CEP-33779, Pacritinib, Ritlecitinib, Fosifidactinib, ZM29923, Ifidancitinib, PAcritinib, Povorctinib, Izencitinib, Coumermycin A1, Nezulcitinib, Gandotinib, NSC 42834, JANEX-1 JAK2/TYK2-IN-1, JAK-IN-1/3/4/5/10/11/14/15/17/18/20, JAK1-IN-4/8/9, JAK2-IN-4/6/7, JAK3-IN-1/6/7/9/11/13/20, JAK-1/3-IN-1, JAK3/BTK-IN-1/2/3/4/5/6, or JAK2/FLT3-IN-1. A dosage of the JAK inhibitor can range from approximately 1.2 grams to approximately 37.6 grams for topical application twice a week and for oral from 10 mg to 100 mg twice a day. In one example, at least a portion of the alternating electric field can be applied to a subject after at least a portion of the JAK inhibitor is delivered. In one example, at least a portion of the alternating electric field can be simultaneously applied with delivering at least a portion of the JAK inhibitor. For example, a portion of the JAK inhibitor can be delivered to the subject at least approximately 5, 10, 15, 20, or 30 minutes before the applying the alternating electric field to a subject. In one example, at least a portion of the alternating electric field can be applied to a subject before at least a portion of the JAK inhibitor is delivered. For example, a portion of the JAK inhibitor can be delivered to the subject at least approximately 1 minute after the applying the alternating electric field to a subject.

In one example, the TYK2 inhibitor can include at least one of Deucravactinib, Cerdulatinib, SAR-20347, BIO, RO495, JAK inhibitor I, GDC046, Ropsactinib, Brepocitinib, Baricitinib, BMS-911543, Oclacitinib, Filgotinib, Abrocitinib, or Solcitinib. A dosage of the TYK2 inhibitor can range from approximately 3 mg to approximately 1600 mg. In one example, at least a portion of the alternating electric field can be applied to a subject after at least a portion of the TYK2 inhibitor is delivered. In one example, at least a portion of the alternating electric field can be simultaneously applied with delivering at least a portion of the TYK2 inhibitor. For example, a portion of the TYK2 inhibitor can be delivered to the subject at least approximately 5, 10, 15, 20, or 30 minutes before the applying the alternating electric field to a subject. In one example, at least a portion of the alternating electric field can be applied to a subject before at least a portion of the TYK2 inhibitor is delivered. For example, a portion of the TYK2 inhibitor can be delivered to the subject at least approximately 1 minute after the applying the alternating electric field to a subject.

In one example, the epithelial differentiation inhibitor can include at least one vitamin D derivative, for example, calcipotriol. A concentration of a topical formulation of the epithelial differentiation inhibitor can range from approximately 0.001% to approximately 0.01%. A dosage of the epithelial differentiation inhibitor can range from approximately 25 g to approximately 100 g per week. In one example, at least a portion of the alternating electric field can be applied to a subject after at least a portion of the epithelial differentiation inhibitor is delivered. In one example, at least a portion of the alternating electric field can be simultaneously applied with delivering at least a portion of the epithelial differentiation inhibitor. For example, a portion of the epithelial differentiation inhibitor can be delivered to the subject at least approximately 5, 10, 15, 20, or 30 minutes before the applying the alternating electric field to a subject. In one example, at least a portion of the alternating electric field can be applied to a subject before at least a portion of the epithelial differentiation inhibitor is delivered. For example, a portion of the epithelial differentiation inhibitor can be delivered to the subject at least approximately 1 minute after the applying the alternating electric field to a subject.

In certain embodiments, more than one inhibitor can be delivered to a subject. For example, at least two, three, four, five, six, seven, eight, nine, or ten inhibitors can be delivered to a subject.

At step 106, the alternating electric field can be delivered to a subject. For example, an alternating electric field (e.g., TTFields) can be applied to target tissue (e.g., tumor or cancer), cells, or an area of a subject. In non-limiting embodiments, the alternating electric field can be applied with predetermined parameters. As an example, the alternating electric field can include a frequency that ranges from about 50 kHz to about 10,000 kHz. As an example, the frequency of the alternating electric field may be between approximately 50 kHz and approximately 1000 kHz or between approximately 100 kHz and approximately 300 kHz. As an example, the frequency of the alternating electric field may be approximately 100 kHz, approximately 150 kHz, approximately 200 kHz, approximately 250 kHz, or approximately 300 kHz. As an example, the alternating electric fields (e.g., TTFields) may include an intensity within a range from about 1 V/cm to about 10 V/cm. As an example, the intensity of the alternating electric field may be between approximately 1 V/cm and approximately 4 V/cm. Other possible exemplary parameters for the alternating electric field may include active time, dimming time, and duty cycle (all of which may be measured in, for example, ms units), among other parameters. The parameters can be modified based on the conditions of the subject (e.g., the sizes of the target tissue, types of tumor, age, or sex of the subject) or the purposes of the treatment. In one example, the intensity of the alternating electric field is between approximately 1 V/cm and approximately 4 V/cm, and the frequency of the alternating electric field is between approximately 150 kHz and approximately 250 kHz for treating tumor/cancer cells. In non-limiting embodiments, the alternating electric field can be applied using two pairs of transducer arrays placed on the subject and directed on a target tissue (e.g., tumor) of the subject.

In certain embodiments, the alternating electric field can be applied to a subject before or after the disclosed inhibitors are applied. In certain embodiments, the alternating electric field (e.g., TTFields) can be simultaneously applied to the target tissue with the disclosed inhibitors. As an example, at least a portion of the applying step 106 may be performed simultaneously/concomitantly with at least a portion of the delivering step 104. In non-limiting embodiments, steps 104 and 106 can be repeated until the desired therapeutic effects are achieved.

Figure 2:
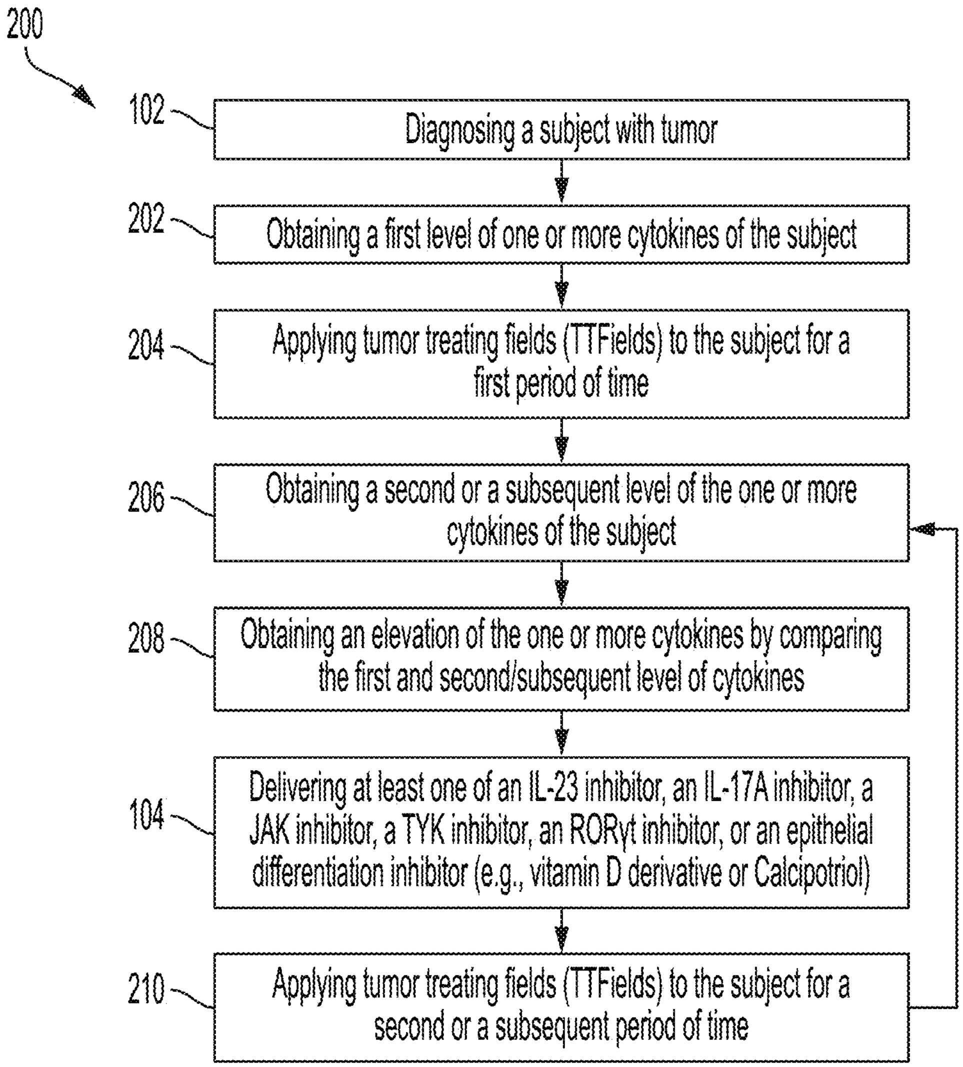
FIG. 2 depicts example approaches for treating a subject in accordance with exemplary embodiments of the present disclosure.

FIG. 2 depicts an example alternative method 200 of treating a subject. Method 200 comprises diagnosing a subject with a disease or disorder (e.g., a tumor) 102, obtaining a first level of one or more cytokines of the subject 202, applying alternating electric fields (e.g., TTFields) to the subject for a first period of time 204, obtaining a second/subsequent level of the one or more cytokines of the subject 206, obtaining an elevation of the one or more cytokines by comparing the first and second/subsequent levels of one of more cytokines 208, delivering at least one of an IL-23 inhibitor, an IL-17A inhibitor, an RORγt inhibitor, a TYK inhibitor, a JAK inhibitor, or an epithelial differentiation inhibitor, e.g., a vitamin D derivative or Calcipotriol 104, and/or applying tumor treating fields (TT-Fields) to the subject for a second period of time 210.

At step 202, a first level of one or more cytokines of a subject can be obtained. The one or more cytokines can include at least one of IL-17A, IL-18, IL-22, or IL-23. The level of the one or more cytokines can be measured through various techniques such as biochemistry (e.g., enzyme-linked immunosorbent assay) and/or proteomic assay (e.g., western blot). In one example, the first level of IL-17A can be between approximately 5 pg/ml to approximately 100 pg/ml. For example, the first level of the IL-17A can be approximately 52 pg/ml. In one example, the first level of IL-23 can be between approximately 10 pg/ml to approximately 600 pg/ml. In one example, the first level of IL-23 can be between approximately 30 pg/ml to approximately 50 pg/ml. For example, the first level of the IL-23 can be approximately 580 pg/ml. In one example, the first level of IL-22 can be between approximately 1 pg/ml to approximately 150 pg/ml. For example, the first level of the IL-22 can be approximately 10 pg/ml.

At step 204, an alternating electric field (e.g., TTFields) can be applied to the subject for a first period of time. The first period of time can be at least approximately 24 hours, 48 hours, or 72 hours. For example, the first period of time can be between approximately 24 hours and approximately 72 hours. The alternating electric field can be continuously or intermittently applied during the first period of time.

At step 206, a second level of the one or more cytokines of the subject can be obtained. The one or more cytokines can include at least one of IL-17A, IL-18, IL-22, or IL-23. The level of the one or more cytokines can be measured through various techniques such as biochemistry (e.g., enzyme-linked immunosorbent assay) and/or proteomic assay (e.g., western blot). At step 208, an elevation of the one or more cytokines can be obtained by comparing the first and second levels to assess the increase of skin irrigation-related factors. In one example, the elevation of the at least one of IL-23, IL-18, IL-17A, or IL-22 can be at least approximately 5%, at least approximately 10%, at least approximately 25%, at least approximately 50%, or at least approximately 100%. For example, the elevation of the IL-23 can be up to approximately 50%. For example, an elevation of the IL-17A, IL-18, or IL-22 can be between approximately 5% to approximately 120%. In non-limiting embodiments, the elevation of the IL-17A can be approximately 90%. In non-limiting embodiments, the first level and second level of the one or more cytokines can be obtained from serum samples of the subject.

In non-limiting embodiments, at least one of the disclosed inhibitors can be delivered to a subject when the elevation of the disclosed one or more cytokines is detected. In one example, the dosage of the disclosed inhibitors can vary based on the elevation level of the disclosed one or more cytokines. For example, the dosage of the disclosed inhibitors can be increased to eliminate, prevent, or decrease the level of the disclosed one or more cytokines in a subject to reduce skin irritation. In one example, the disclosed inhibitors can be delivered to the subject that shows the elevation of at least one of the IL-23, IL-18, IL-17A, or IL-22 prior to delivering another alternating electric fields treatment.

In non-limiting embodiments, the elevation of the disclosed one or more cytokines can be obtained before applying the alternating electric fields. For example, the elevation of the disclosed one or more cytokines can be obtained by comparing the first level of the disclosed one or more cytokines with a known normal range of the one or more cytokines, which does not cause skin irritation. For example, the normal level of IL-17A can be between approximately 1 pg/ml and approximately 50 pg/ml. In one example, the normal level of the IL-17A can be approximately 20 pg/ml. In one example, the normal level of IL-23 can be between approximately 10 pg/ml to approximately 600 pg/ml. In one example, the normal level of IL-23 can be between approximately 30 pg/ml to approximately 50 pg/ml. For example, the normal level of the IL-23 can be approximately 580 pg/ml. In one example, the normal level of IL-22 can be between approximately 1 pg/ml to approximately 10 pg/ml. For example, the normal level of IL-22 can be approximately 3 pg/ml. In one example, the normal level of IL-18 can be between approximately 50 pg/ml to approximately 10,000 pg/ml. In one example, the normal level of IL-18 can be approximately 155 pg/ml. In one example, the elevation of the at least one of IL-23, IL-17A, or IL-22 can be at least approximately 5%, at least approximately 10%, at least approximately 25%, at least approximately 50%, at least approximately 100%, or at least approximately 150% between the first level and the normal level. For example, the elevation of the IL-23 can be up to approximately 50%. For example, an elevation of the IL-17A can be between approximately 5% to approximately 120%. In non-limiting embodiments, the elevation of the IL-17A can be approximately 90%. In one example, the disclosed inhibitors can be delivered to the subject that shows the elevation of at least one of the IL-23, IL-17A, or IL-22 prior to delivering the disclosed alternating electric field.

At step 210, the alternating electric field (e.g., TTFields) can be applied to the subject for a second period of time. The second period time can be at least approximately 24 hours, 48 hours, or 72 hours. For example, the second period of time can be between approximately 24 hours and approximately 48 hours. The alternating electric field can be continuously or intermittently applied during the second period.

Experimental Results

The application of the alternating electric fields (e.g., TTFields) causes skin irritation by promoting the release of inflammatory cytokines and/or proteins. Using certain embodiments disclosed herein, alternating electric field (e.g., TTFields) was applied to a subject. Various mouse models were exposed to alternating electric fields. For example, an orthotopic ovarian cancer mice model was established by injecting the MOSE-L-ffl cancer cells into 12-week-old female mice. Mice were treated with alternating electric fields (e.g., TTFields, 200 kHz) for 10 days with the field intensity at least 1V/cm using the INOVIVO system (Novocure, Haifa, Israel). At the endpoint of the treatment, blood samples were collected in designated blood serum tubes for immunoassay analysis.

Lewis Lung Carcinoma (LLC) model ovarian cancer mice model was established. Mice were treated with alternating electric fields (e.g., TTFields. 150 kHz) for 10 days with the field intensity (at least 1V/cm) using the INOVIVO system (Novocure, Haifa, Israel). At the endpoint of the treatment, blood samples were collected in designated blood serum tubes. Safety rats (controls) were treated with 150 kHz for 14 days with field intensity (at least 1V/cm) using the INOVIVO system (Novocure, Haifa, Israel).

The disclosed results suggest an upregulation of the IL-17A/IL-23 level that can indicate increased inflammation of the skin as seen in psoriasis patients and that administering IL17A/IL23 inhibitors to patients can be beneficial in treating skin irritation.

IL-23 heterodimer is formed by the combination of the p19 and p40 subunits and possesses the most structural similarity to IL-12. A key immunologic function of IL-23 is to drive the differentiation process of naïve T-helper (Th) cells into Th17 cells, primary producers of IL-17. IL-23 inhibits the differentiation of regulatory T (Treg) cells that produce IL-10 and inhibit inflammation and thus restrict Th17 differentiation. IL-23 promotes the Th17 cells to secrete IL-17, IL-22, and TNF-α.

The IL-23/IL-17A pathway plays an important role in skin irritation. Keratinocytes constitutively express IL-23. Keratinocytes in psoriatic skin expressed higher levels of IL-23 compared with keratinocytes in normal skin. Psoriasis, hidradenitis suppurativa, atopic dermatitis, and alopecia areata are the T-cell immune axis and cytokines in the pathogenesis of skin inflammation. T helper cells (including Th1, Th17, and Th22) are the primary producers of IL-22. The IL-22-IL-22 subunit (IL-22R1) axis has shown a high potential clinical relevance in inflammatory diseases like psoriasis, ulcerative colitis, liver and pancreatic damage, graft-versus-host disease, certain infections, and tumors. Upon Skin inflammation, an increase in IL-22 aids Keratinocyte proliferation. Th17-type cytokines (IL-17A, IL-17F and IL-22) drive keratinocyte hyperproliferation and chemokine production and perpetuate further leukocyte recruitment. IL-17-targeting biologics can reduce the disease burden of psoriasis in patients with moderate-to-severe disease.

FIGS. 3A-3D depict the thicker epidermis generation in the skin below electrodes for applying the alternating electric fields (e.g., TTFields). Skin sections were derived from safety experiments where male and female rats were treated with alternating electric fields (e.g., TTFields, 150 kHZ) for two weeks. As shown in FIG. 3A, skin sections were taken from the skin under the electrodes and control skin (without electrodes) and stained with an anti-17A antibody. As shown in FIGS. 3B-3D, results show an increase in IL-17A staining and epidermis thickness in the skin under the electrode compared to the control skin. Furthermore, an increase in IL-23 in the skin under electrode compared to the no treatment group and control skin (sham model). There are certain inhibitors that can be used to reduce the skin irritation caused by the application of the alternating electric fields (e.g., TTFields), such as IL-17 inhibitors (e.g., secukinumab, ixekizumab, and brodalumab) and IL-23 inhibitors (e.g., guselkumab, risankizumab, and tildrakizumab).

As shown in FIGS. 3A-3C, in skin samples derived from the safety experiment rats, results showed an increase in IL-17A expression in the skin under the electrode compared to skin not under the electrode. Also, epidermal thickness in the skin under the electrode was significantly higher than in skin not under the electrode suggesting a hyperproliferation of keratinocytes.

As shown in FIG. 3D, in serum samples derived from rats, a certain trend showed an increase in both cytokines (i.e., levels of IL-17A and IL-23 in serum) following the alternating electric fields (e.g., TTFields) application compared to heat sham.

Secukinumab, ixekizumab and brodalumab are monoclonal antibody therapies that inhibit interleukin (IL)-17 activity and can be widely used for the treatment of psoriasis, psoriatic arthritis, and ankylosing spondylitis. Inhibitors of interleukin-23 (e.g., ustekinumab, guselkumab, tildrakizumab, and risankizumab) can be safe and effective options for the treatment of moderate-to-severe plaque psoriasis. Ustekinumab can be used for treating psoriatic arthritis. IL-23 and IL-17A inhibitors can be administered by subcutaneous injection every few weeks.

Certain IL-23 and IL-17A inhibitors have a large molecular weight that makes them unsuitable for the use as topical medicines because they cannot diffuse across the skin barrier. There are topical RORγt inhibitors to treat psoriasis now in clinical trials, such as JNJ-61803534 and GSK2981278. The IL-23 and IL-17A inhibitors can include a topical JAK inhibitor, TYK2 inhibitor, or calcipotriol.

Figure 4A:
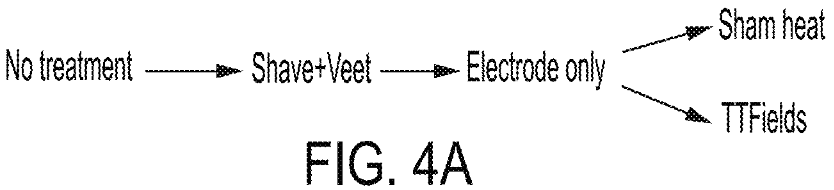
FIGS. 4A-4D depict the effects of the alternating electric fields (e.g., TTFields) on epidermal thickening and the release of IL-17A in the no treatment, shave and veet only, electrode only, sham heat, and alternating electric fields applied groups.

FIGS. 4A-4D depict the effects of the alternating electric fields (e.g., TTFields) on epidermal thickening and elevation of IL-17A in various groups (i.e., no treatment, shave and veet only, electrode only, sham heat, and alternating electric fields (e.g., TTFields). As shown in FIG. 4A, mice in the no-treatment group did not receive any treatment. The hair of the mice in the shave and the veet-only group was physically and chemically removed. In the Electrode group, the hair of the mice was physically/chemically removed, and then electrodes were applied without heat or alternating electric fields (e.g., TTFields). In the sham heat model group, the electrodes with only heat were applied to the mice with hair removed. In the alternating electric fields (e.g., TTFields) group, the TTFields were applied to the mice (with hair removed) through the electrodes.

Figure 4B:
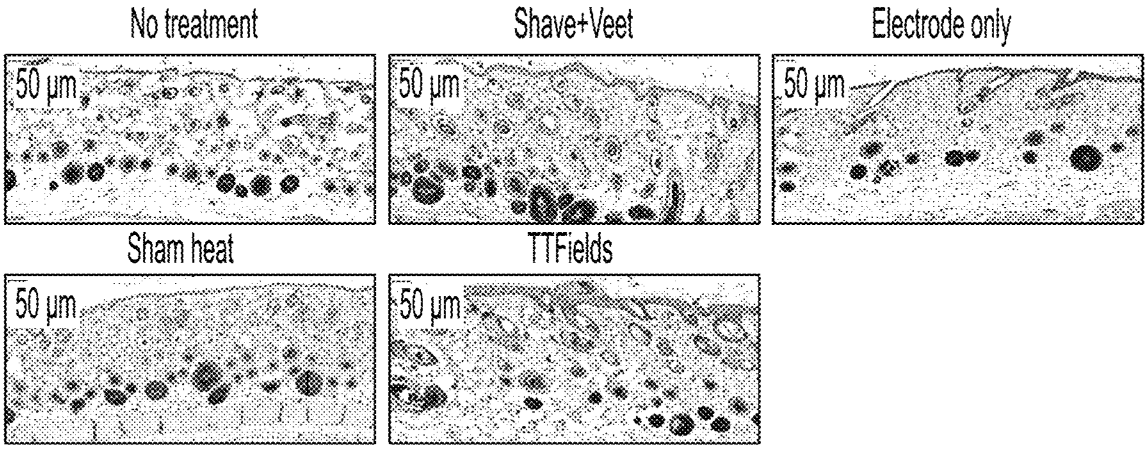
Figure 4C:
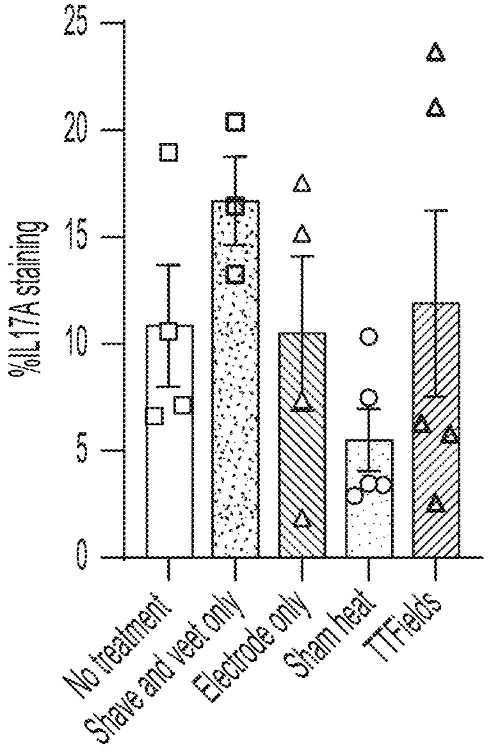
Figure 4D:
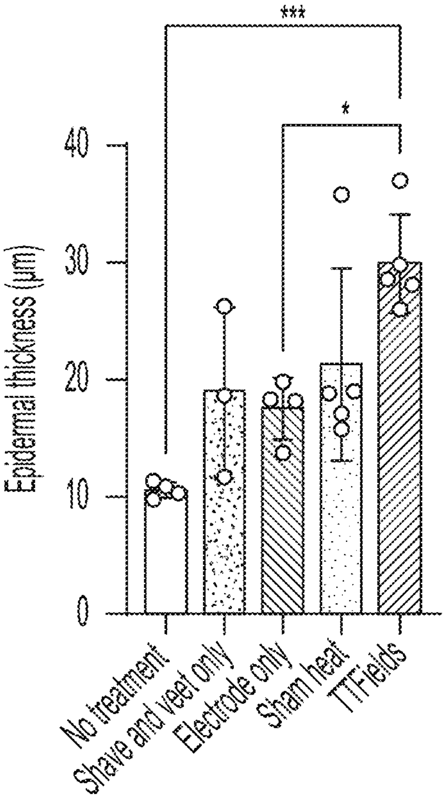

The skin under the alternating electric fields (e.g., TTFields) was compared to untreated skin, sham heat, skin only treated with shave and Veet, and skin that had been treated with shave and Veet to which an electrode was placed without connection to alternating electric fields (e.g., TTFields) or heat. As shown in FIG. 4B, skin sections were taken from the no treatment, shave and veet only, electrode only, sham heat, and alternating electric fields (e.g., TTFields) groups and stained with an anti-17A antibody. An increase in epidermal thickness in alternating electric fields (e.g., TTFields) was detected compared to untreated mice. There was a significant increase in alternating electric fields (e.g., TTFields) treated skin compared to all control groups. As shown in FIGS. 4C and 4D, results show an increase in epidermis thickness in the skin under alternating electric fields (e.g., TTFields) compared to the no treatment, shave and veet only, electrode only, and sham heat groups. An increase in IL-17A staining in the alternating electric fields (e.g., TTFields) group was detected compared to the sham heat group.

Figure 5A:
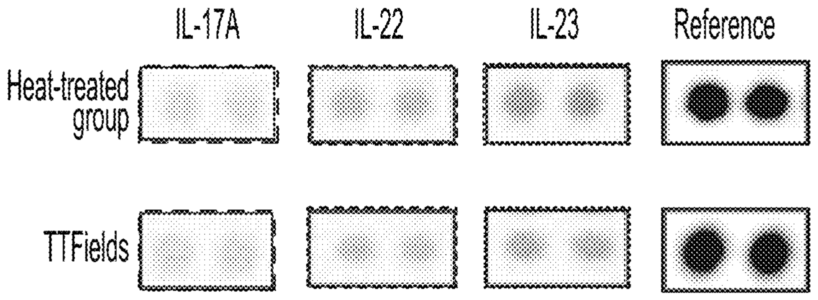
FIGS. 5A-5B depict example effects of alternating electric fields on the release of IL-17A, IL-22, and IL-23 in an ovarian cancer model.
Figure 5B:
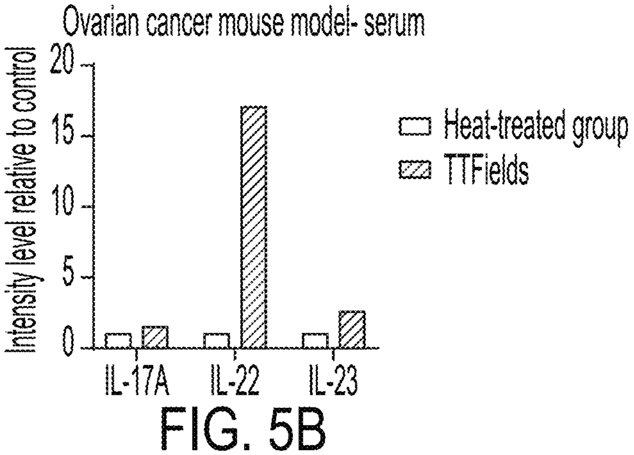

FIGS. 5A-5B depict the effects of alternating electric fields (e.g., TTFields) on the release of IL-17A, IL-22, and IL-23 in an ovarian tumor model. Mice were orthotopically implanted with MOSE-FFL cells. During the following 15 days, alternating electric fields (e.g., TTFields) were applied to mice using a torso array at 200 kHz for 10 days. Serums were derived, and a cytokine array was performed. FIGS. 5A and 5B show an increase in circulating levels of IL-17A, IL-22 and IL-23 in mice treated with alternating electric fields (e.g., TTFields) compared to heat-treated group.

Figure 6:
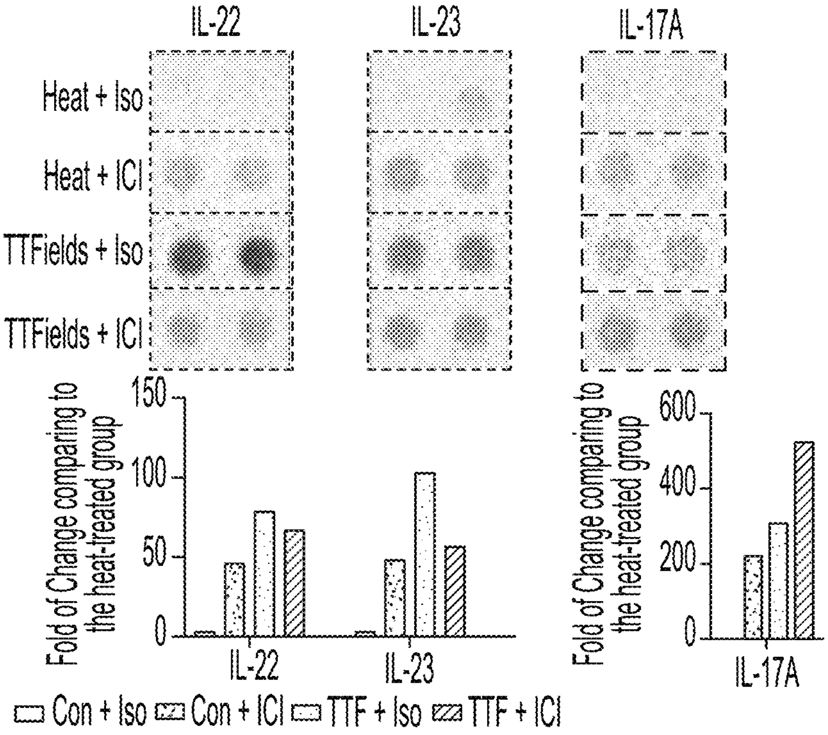
FIG. 6 depicts the example effects of alternating electric fields on the release of IL-17A, IL-22, and IL-23 in an LLC-2 tumor model.

FIG. 6 depicts the effects of alternating electric fields (e.g., TTFields) on the release of IL-17A, IL-22, and IL-23 in an LLC-2 tumor model. Mice were orthotopically implanted with LLC-2 cells. During the following 7 days, alternating electric fields (e.g., TTFields) were applied to mice using a torso array at 150 kHz for 10 days. Serums were derived, and a cytokine array was performed. FIG. 6 shows an increase in circulating levels of IL-17A, IL-22, and IL-23 in mice treated with alternating electric fields (e.g., TTFields) compared to heat-treated group.

Figure 7A:
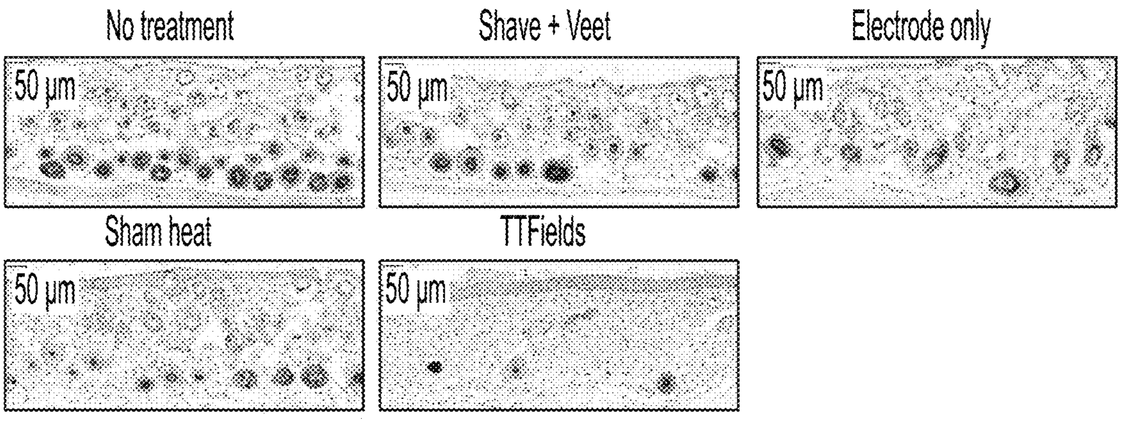
FIGS. 7A and 7B depict the epidermal proliferation in the no treatment, shave and veet only, electrode only, sham heat, and alternating electric fields applied groups.
Figure 7B:
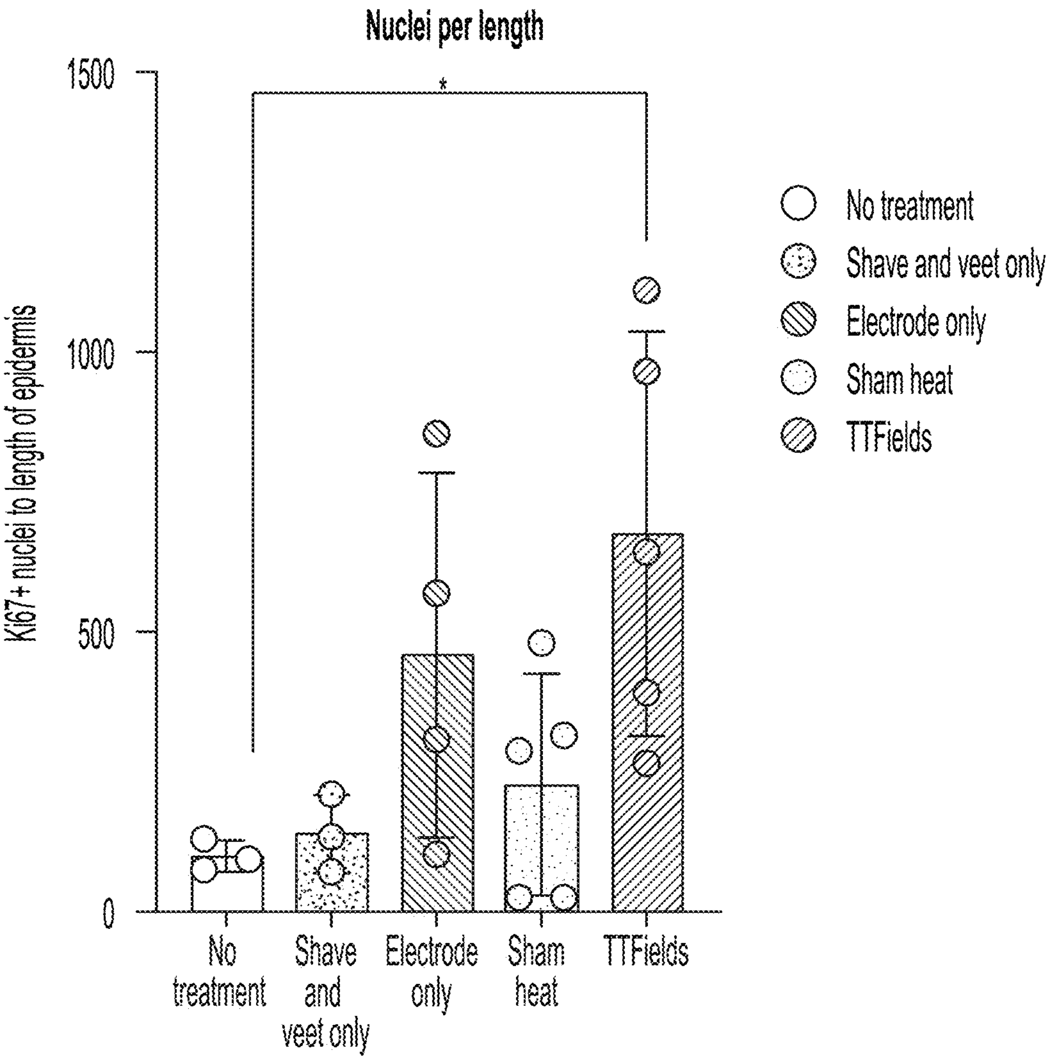

FIGS. 7A and 7B depict the effects of alternating electric fields (e.g., TTFields) on epidermal proliferation as a marker for quick epidermal turnover indicating an increase in epidermal differentiation. FIG. 7A shows the skin sections of various groups stained by Ki67, a marker for epidermal cell proliferation. FIG. 7B provides the quantification results showing the Ki67 positive nuclei in the epidermis per length in various groups. The results show an increase in epidermal proliferation in the alternating electric fields (e.g., TTFields) treated epidermis compared to no treatment groups.

IL-22 can increase when there is skin injury, and the rise in IL-22 can be caused by increased epidermal differentiation-hyper proliferation. Calcipotriol, tofacitinib 2% Cream or opzelura can be used to treat the epidermal differentiation and thickening of epidermis that are caused by a quick turnover of skin following the wound healing process. The quick turnover caused by alternating electric fields can result in inflammation and thickening of the epidermis (but frail skin). Accordingly, Calcipotriol, tofacitinib 2% Cream or opzelura can also be used for treating the skin irritation caused by alternating electric fields (e.g., TTFields).

Figure 8A:
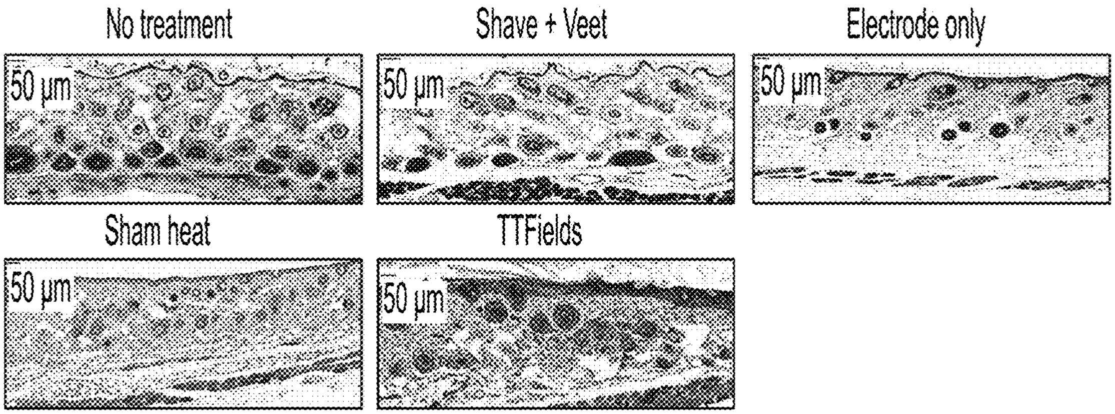
FIGS. 8A-8C depict the example effects of alternating electric fields on epidermis thickness in the skin (FIG. 8A) and the release of IL-22 in the epidermal staining (FIG. 8B) and skin section (FIG. 8C) compared to the no treatment, shave and veet only, electrode only, and sham heatgroups.
Figure 8B:
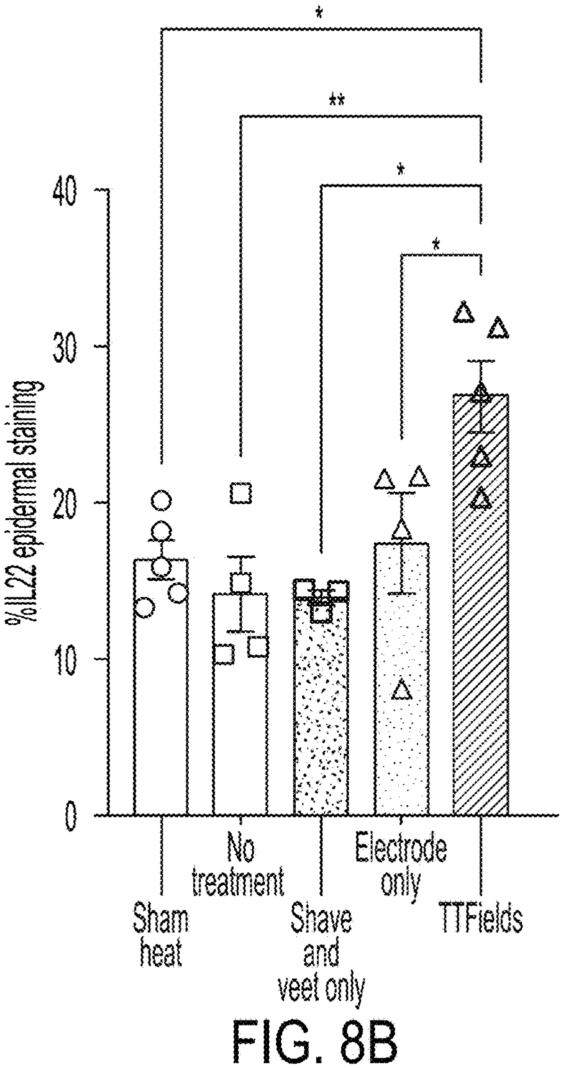
Figure 8C:
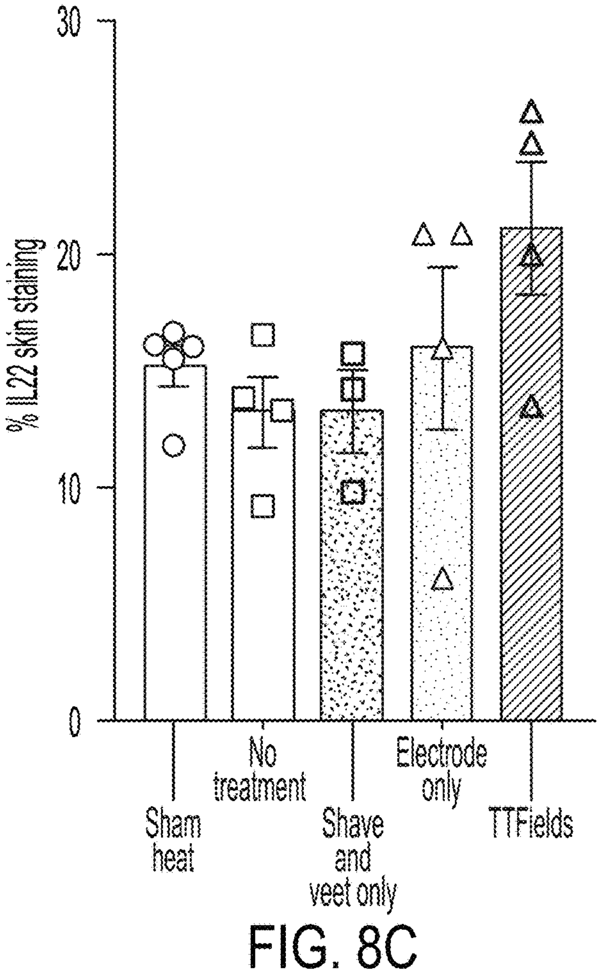

FIGS. 8A-8C depict the effects of alternating electric fields (e.g., TTFields) on epidermal thickening and elevation of IL-22 in various groups (i.e., no treatment, shave and veet only, electrode only, sham heat, and alternating electric fields (e.g., TTFields). As shown in FIG. 8A, skin sections were taken from the no treatment, shave and veet only, electrode only, sham heat, and alternating electric fields (e.g., TTFields) groups and stained with an anti-IL22 antibody. A significant increase of IL-22 in epidermal staining in the alternating electric fields (e.g., TTFields) applied group was detected compared to other groups (e.g., no treatment, shave and veet only, electrode only, and sham heat groups. There was a significant increase in the thickness of the epidermis in the alternating electric fields (e.g., TTFields)-applied groups compared to all other experimental groups. As shown in FIG. 8A, results show an increase in epidermis thickness in the skin under alternating electric fields (e.g., TTFields) compared to the no treatment, shave and veet only, electrode only, and sham heat groups. An increase in IL-22 staining in the alternating electric fields (e.g., TTFields) group was detected compared to the sham heat group. FIG. 8B shows a significant increase in IL-22 epidermal staining following alternating electric fields (e.g., TTFields) compared to all other experimental groups. FIG. 8C shows an increase in IL-22 staining in skin sections following alternating electric fields (e.g., TTFields) compared to all other experimental groups.

Exemplary Apparatuses

Figure 9:
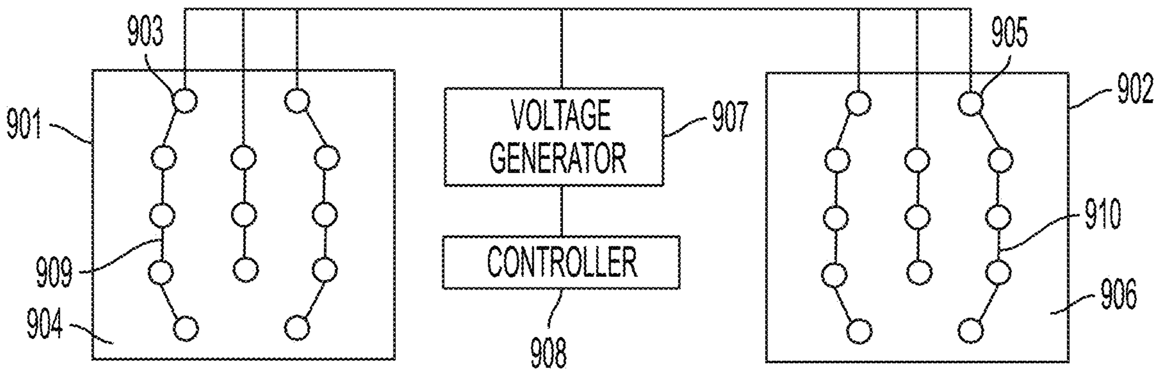
FIG. 9 depicts one example of an apparatus to apply alternating electric fields with modulated electric fields to a subject's body.

FIG. 9 depicts one example of an apparatus to apply alternating electric fields (e.g., TTFields) to a subject's body. The first transducer array 901 includes 13 electrode elements 903, which are positioned on the substrate 904, and the electrode elements 903 are electrically and mechanically connected to one another through a conductive wiring 909. The second transducer array 902 includes 13 electrode elements 905, which are positioned on the substrate 906, and the electrode elements 905 are electrically and mechanically connected to one another through a conductive wiring 910. The first transducer array 901 and the second transducer array 902 are connected to an AC voltage generator 907 and a controller 908. The controller 908 may include one or more processors and memory accessible by the one or more processors. The memory may store instructions that when executed by the one or more processors, control the AC voltage generator 907 to implement one or more embodiments of the invention. In some embodiments, the AC voltage generator 907 and the controller 908 may be integrated in the first transducer array 901 and the second transducer array 902 and form a first electric field generator and a second electric field generator.

Figure 10:
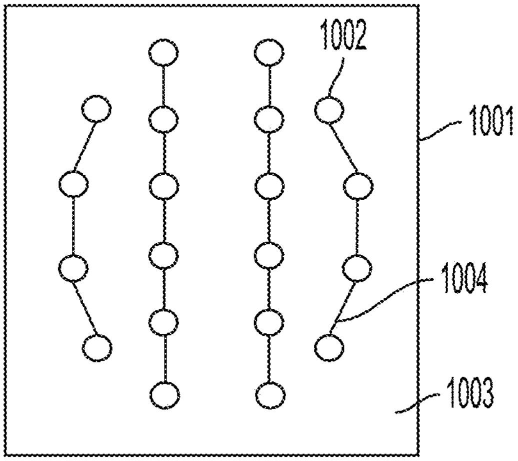
FIG. 10 depicts an example structure of a transducer array.

FIG. 10 depicts one example of an alternative design of the transducer array. The transducer array 1001 includes 20 electrode elements 1002, which are positioned on the substrate 1003, and the electrode elements 1002 are electrically and mechanically connected to one another through a conductive wiring 1004.

Figure 11:
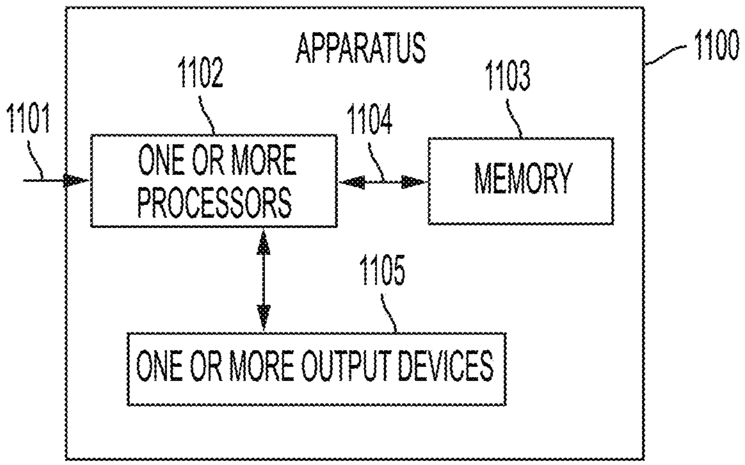
FIG. 11 depicts an example computer apparatus.

FIG. 11 depicts an example computer apparatus for use with the embodiments herein. As an example, the apparatus 1100 may be a computer to implement certain inventive techniques disclosed herein. As an example, the apparatus 1100 may be a controller apparatus to apply the alternating electric fields (e.g., TTFields) with modulated electric fields for the embodiments herein. The controller apparatus 1100 may be used as the controller 908 of FIG. 9. The apparatus 1100 may include one or more processors 1102, memory 1103, one or more input devices, and one or more output devices 1105.

In one example, based on input 1101, the one or more processors generate control signals to control the voltage generator to implement an embodiment of the invention. In one example, the input 1101 is user input. In another example, the input 1101 may be from another computer in communication with the controller apparatus 1100. The input 1101 may be received in conjunction with one or more input devices (not shown) of the apparatus 1100.

The output devices 1105 may provide the status of the operation of the invention, such as transducer array selection, voltages being generated, and other operational information. The output device(s) 1105 may provide visualization data according to certain embodiments of the invention.

The memory 1103 is accessible by the one or more processors 1102 (e.g., via the link 1104) so that the one or more processors 1102 can read information from and write information to the memory 1103. The memory 1103 may store instructions that when executed by the one or more processors 1102 implement one or more embodiments of the invention. The memory 1103 may be a non-transitory processor readable medium containing a set of instructions thereon, wherein when executed by a processor (such as one or more processors 1102), the instructions cause the processor to perform one or more methods disclosed herein.

The apparatus 1100 may be an apparatus including: one or more processors (such as one or more processors 1102); and memory (such as memory 1103) accessible by the one or more processors, the memory storing instructions that when executed by the one or more processors, cause the apparatus to perform one or more methods disclosed herein.

Illustrative Embodiments

The invention includes other illustrative embodiments, such as the following.

Illustrative Embodiment 1. A method of treating a subject, comprising: delivering an interleukin 17A (IL-17A) inhibitor to the subject and applying an alternating electric field to the subject at a frequency between approximately 50 kHz and approximately 10,000 kHz.

Illustrative Embodiment 2. The method of Illustrative Embodiment 1, wherein the subject has a tumor, and the alternating electric field is applied to the tumor of the subject.

Illustrative Embodiment 3. The method of Illustrative Embodiment 1, wherein the IL-17A inhibitor comprises at least one of secukinumab, ixekizumab, and brodalumab.

Illustrative Embodiment 4. The method of Illustrative Embodiment 1, wherein at least a portion of the alternating electric fields applying step is performed after at least a portion of the interleukin 17A inhibitor delivering step.

Illustrative Embodiment 5. The method of Illustrative Embodiment 1, wherein at least a portion of the alternating electric fields applying step is performed simultaneously with at least a portion of the interleukin 17A inhibitor delivering step.

Illustrative Embodiment 6. The method of Illustrative Embodiment 1, wherein at least a portion of the applying step is performed before at least a portion of the delivering step.

Illustrative Embodiment 7. A method of treating a subject, comprising: delivering a RAR-related orphan receptor gamma (RORγt) inhibitor to the subject and applying an alternating electric field to the subject at a frequency between approximately 50 kHz and approximately 10,000 kHz.

Illustrative Embodiment 8. The method of Illustrative Embodiment 7, wherein the subject has a tumor, and the alternating electric field is applied to the tumor of the subject.

Illustrative Embodiment 9. The method of Illustrative Embodiment 7, wherein the RORγt inhibitor comprises at least one of JNJ-61803534 or GSK2981278.

Illustrative Embodiment 10. The method of Illustrative Embodiment 7, wherein the alternating electric field is applied at a frequency between approximately 50 kHz and approximately 1,000 kHz.

Illustrative Embodiment 11. The method of Illustrative Embodiment 10, wherein the alternating electric field is applied at a frequency between approximately 100 kHz and approximately 300 kHz.

Illustrative Embodiment 12. The method of Illustrative Embodiment 7, wherein the alternating electric field is applied using two pairs of transducers placed on the subject and directed on a tumor of the subject.

Illustrative Embodiment 13. A method for treating a subject, comprising: delivering an interleukin 23 (IL-23) inhibitor to the subject and applying an alternating electric field to the subject at a frequency between approximately 50 kHz and approximately 10,000 kHz.

Illustrative Embodiment 14. The method of Illustrative Embodiment 13, wherein a portion of the IL-23 inhibitor is delivered to the subject at least 5 minutes before the alternating electric fields applying step.

Illustrative Embodiment 15. The method of Illustrative Embodiment 13, wherein the alternating electric field is applied from approximately 18 hours to approximately 96 hours, and the IL-23 inhibitor is applied at least one time during the alternating electric fields applying step.

Illustrative Embodiment 16. The method of Illustrative Embodiment 13, wherein a portion of the IL-23 inhibitor is delivered to the subject approximately two days after the alternating electric fields applying step.

Illustrative Embodiment 17. The method of Illustrative Embodiment 13, wherein a portion of the IL-23 inhibitor is delivered to the subject approximately two days after the alternating electric fields applying step, wherein a dosage of the IL-23 inhibitor ranges from 5 mg to 200 mg.

Illustrative Embodiment 18. The method of Illustrative Embodiment 13, further comprising: prior to delivering the IL-23 inhibitor to the subject, obtaining a first level of at least one of IL-23, IL-17A, or IL-22 in the subject; obtaining a second level of at least one of IL-23, IL-17A, or IL-22 in the subject after the applying the alternating electric filed to the subject; detecting an elevation of the at least one of IL-23, IL-17A, or IL-22 by comparing the first and second levels of at least one of IL-23, IL-17A, or IL-22; and delivering the IL-23 inhibitor to the subject based on the elevation of the at least one of IL-23, IL-17A, or IL-22.

Illustrative Embodiment 19. The method of Illustrative Embodiment 18, wherein the elevation of the at least one of IL-23, IL-17A, or IL-22 is at least approximately 5%.

Illustrative Embodiment 20. The method of Illustrative Embodiment 18, further comprising delivering an inhibitor to the subject, which shows the elevation of at least one of IL-23, IL-17A, or IL-22 prior to delivering another alternating electric field, wherein the inhibitor comprises at least one of an IL-23 inhibitor, an IL-17A inhibitor, a RAR-related orphan receptor gamma (RORγt) inhibitor, an IL-17F inhibitor, an IL-17RA inhibitor, an IL-12Rβ1 inhibitor, an IL-23R inhibitor, an IL-22 inhibitor, a Janus kinase (JAK) inhibitor, a non-receptor tyrosine-protein kinase (TYK2) inhibitor, or an inhibitor of epithelial differentiation.

Illustrative Embodiment 20a. The method of Illustrative Embodiment 20, wherein the inhibitor of epithelial differentiation is a vitamin D derivative, optionally calcipotriol.

Illustrative Embodiment 21. The method of Illustrative Embodiment 18, wherein the first level of the IL-23 is approximately 30 pg/ml to approximately 50 pg/ml.

Illustrative Embodiment 22. The method of Illustrative Embodiment 21, wherein the first level of the IL-23 is approximately 580 pg/ml.

Illustrative Embodiment 23. The method of Illustrative Embodiment 18, wherein the elevation of the IL-23 is up to approximately 50%.

Illustrative Embodiment 24. The method of Illustrative Embodiment 1, further comprising: prior to delivering the IL-23 inhibitor to the subject, obtaining a first level of at least one of IL-23, IL-17A, or IL-22 in the subject; obtaining a second level of at least one of IL-23, IL-17A, or IL-22 in the subject after the applying the alternating electric filed to the subject, detecting an elevation of the at least one of IL-23, IL-17A, or IL-22 by comparing the first and second levels of at least one of IL-23, IL-17A, or IL-22; and delivering the IL-23 inhibitor to the subject based on the elevation of the at least one of IL-23, IL-17A, or IL-22.

Illustrative Embodiment 25. The method of Illustrative Embodiment 1, wherein the elevation of the at least one of IL-23, IL-17A, or IL-22 is at least approximately 5%.

Illustrative Embodiment 26. The method of Illustrative Embodiment 1, further comprising delivering an inhibitor to the subject, which shows the elevation of at least one of IL-23, IL-17A, or IL-22 prior to delivering another alternating electric field, wherein the inhibitor comprises at least one of an IL-23 inhibitor, an IL-17A inhibitor, a RAR-related orphan receptor gamma (RORγt) inhibitor, an IL-17F inhibitor, an IL-17RA inhibitor, an IL-12Rβ1 inhibitor, an IL-23R inhibitor, an IL-22 inhibitor, a Janus kinase (JAK) inhibitor, a non-receptor tyrosine-protein kinase (TYK2) inhibitor, or an inhibitor of epithelial differentiation.

Illustrative Embodiment 27. The method of Illustrative Embodiment 24, wherein the first level of the IL-17A is approximately 5 pg/ml to approximately 100 pg/ml.

Illustrative Embodiment 28. The method of Illustrative Embodiment 27, wherein the first level of the IL-17A is approximately 52 pg/ml.

Illustrative Embodiment 29. The method of Illustrative Embodiment 25, wherein an elevation of the IL-17A is approximately 5% to approximately 120%.

Illustrative Embodiment 30. The method of Illustrative Embodiment 25, wherein an elevation of the IL-17A is approximately 90%.

Illustrative Embodiment 31. The method of Illustrative Embodiment 1, wherein the period of time for applying the alternating electric field to the subject is at least approximately 3 days.

Illustrative Embodiment 32. The method of Illustrative Embodiment 1, wherein the IL-17A inhibitor is formulated for topical, oral, or parenteral administration, wherein the IL-17A inhibitor is formulated as a gel, a hydrogel, a gel containing nanoparticles, an adhesive band, or a band-aid.

Illustrative Embodiment 33. The method of Illustrative Embodiment 1, wherein a portion of the IL-17A inhibitor is delivered to the subject approximately 30 minutes before the alternating electric fields applying step.

Illustrative Embodiment 34. The method of Illustrative Embodiment 1, wherein the alternating electric field is applied between approximately 18 hours and approximately 48 hours, and the IL-17A inhibitor is applied at least one time during the alternating electric fields applying step.

Illustrative Embodiment 35. The method of Illustrative Embodiment 1, wherein a portion of the IL-17A inhibitor is delivered to the subject approximately 30 minutes after the alternating electric fields applying step.

Illustrative Embodiment 36. The method of Illustrative Embodiment 1, wherein a dosage of the IL-17A inhibitor range from approximately 100 mg to approximately 300 mg.

Illustrative Embodiment 37. The method of Illustrative Embodiment 7, wherein the RORγt inhibitor is formulated for topical, oral, or parenteral administration.

Illustrative Embodiment 38. The method of Illustrative Embodiment 7, wherein at least a portion of the alternating electric fields applying step is performed after at least a portion of the delivering step.

Illustrative Embodiment 39. The method of Illustrative Embodiment 7, wherein a portion of the RORγt inhibitor is delivered to the subject approximately 30 minutes before the applying step.

Illustrative Embodiment 40. The method of Illustrative Embodiment 7, wherein at least a portion of the applying step is performed simultaneously with at least a portion of the RORγt inhibitor delivering step.

Illustrative Embodiment 41. The method of Illustrative Embodiment 7, wherein the alternating electric field is applied from approximately 18 hours to approximately 96 hours, and the RORγt inhibitor is delivered at least one time during the applying step.

Illustrative Embodiment 42. The method of Illustrative Embodiment 7, wherein at least a portion of the alternating electric field applying step is performed before at least a portion of the RORγt inhibitor delivering step.

Illustrative Embodiment 43. The method of Illustrative Embodiment 7, wherein a portion of the RORγt inhibitor is delivered to the subject approximately 30 minutes after the alternating electric field applying step.

Illustrative Embodiment 44. The method of Illustrative Embodiment 7, wherein a dosage of the RORγt inhibitor range from approximately 5 mg to approximately 600 mg.

Illustrative Embodiment 45. The method of Illustrative Embodiment 26, wherein the JAK inhibitor comprises at least one of Opzelura or Tofacitinib.

Illustrative Embodiment 46. An interleukin 23 (IL-23) inhibitor for use in a method of reducing skin irritation in a subject caused by application of an alternating electric field, the method comprising: delivering an interleukin 23 (IL-23) inhibitor to the subject and applying an alternating electric field to the subject at a frequency between approximately 50 kHz and approximately 10,000 kHz.

Illustrative Embodiment 47. The IL-23 inhibitor for use of Illustrative Embodiment 47, wherein the IL-23 inhibitor comprises at least one of guselkumab, risankizumab, and tildrakizumab.

Illustrative Embodiment 48. The IL-23 inhibitor for use of Illustrative Embodiment 47, further comprising: prior to delivering the IL-23 inhibitor to the subject, obtaining a first level of at least one of IL-23, IL-17A, or IL-22 in the subject; obtaining a second or a subsequent level of at least one of IL-23, IL-17A, or IL-22 in the subject after the applying the alternating electric field to the subject; detecting an elevation of the at least one of IL-23, IL-17A, or IL-22 by comparing the first and second or a subsequent levels of at least one of IL-23, IL-17A, and IL-22; and delivering the IL-23 inhibitor to the subject based on the elevation of the at least one of IL-23, IL-17A, and IL-22.

Illustrative Embodiment 49. The IL-23 inhibitor for use of any one of Illustrative Embodiments 46-48, wherein the elevation of the at least one of IL-23, IL-17A, or IL-22 is at least approximately 5%.

Illustrative Embodiment 50. The IL-23 inhibitor for use of Illustrative Embodiment 49, further comprising: delivering an inhibitor to the subject who shows the elevation of at least one of IL-23, IL-17A, and IL-22 prior to delivering another alternating electric field, wherein the inhibitor comprises at least one of an IL-23 inhibitor, an IL-17A inhibitor, an RAR-related orphan receptor gamma (RORγt) inhibitor, an IL-17F inhibitor, an IL-17RA inhibitor, an IL-12Rβ1 inhibitor, an IL-23R inhibitor, an IL-22 inhibitor, a Janus kinase (JAK) inhibitor, a non-receptor tyrosine-protein kinase (TYK2) inhibitor, and a vitamin D derivative.

Illustrative Embodiment 51. The IL-23 inhibitor of Illustrative Embodiment 46, wherein at least a portion of the alternating electric field applying step is performed before, simultaneously, or after at least a portion of the interleukin 23 (IL-23) inhibitor delivering step.

Illustrative Embodiment 52. An interleukin 17A (IL-17A) inhibitor for use in a method of reducing skin irritation in a subject caused by application of an alternating electric field, the method comprising: delivering an interleukin 17A (IL-17A) inhibitor to the subject and applying an alternating electric field to the subject at a frequency between approximately 50 kHz and approximately 10,000 kHz.

Illustrative Embodiment 53. The method of Illustrative Embodiment 52, wherein the IL-17A inhibitor comprises at least one of secukinumab, ixekizumab, and brodalumab.

Illustrative Embodiment 54. A RAR-related orphan receptor gamma (RORγt) inhibitor for use in a method of reducing skin irritation in a subject caused by application of an alternating electric field, the method comprising: delivering a RAR-related orphan receptor gamma (RORγt) inhibitor to the subject and applying an alternating electric field to the subject at a frequency between approximately 50 kHz and approximately 10,000 kHz.

Illustrative Embodiment 55. The method of Illustrative Embodiment 54, wherein the RORγt inhibitor comprises at least one of JNJ-61803534 and GSK2981278.

Illustrative Embodiment 56. An interleukin 17F (IL-17F) inhibitor for use in a method of reducing skin irritation in a subject caused by application of an alternating electric field, the method comprising: delivering an interleukin 17F (IL-17F) inhibitor to the subject and applying an alternating electric field to the subject at a frequency between approximately 50 kHz and approximately 10,000 kHz.

Illustrative Embodiment 57. An interleukin 17RA (IL17RA) inhibitor for use in a method of reducing skin irritation in a subject caused by application of an alternating electric field, the method comprising: delivering an interleukin 17RA (IL17RA) inhibitor to the subject and applying an alternating electric field to the subject at a frequency between approximately 50 kHz and approximately 10,000 kHz.

Illustrative Embodiment 58. An interleukin 12Rβ1 (IL-12Rβ1) inhibitor for use in a method of reducing skin irritation in a subject caused by application of an alternating electric field, the method comprising: delivering an interleukin 12Rβ1 (IL-12Rβ1) inhibitor to the subject and applying an alternating electric field to the subject at a frequency between approximately 50 kHz and approximately 10,000 kHz.

Illustrative Embodiment 59. An interleukin 23R (IL-23R) inhibitor for use in a method of reducing skin irritation in a subject caused by application of an alternating electric field, the method comprising: delivering an interleukin 23R (IL-23R) inhibitor to the subject and applying an alternating electric field to the subject at a frequency between approximately 50 kHz and approximately 10,000 kHz.

Illustrative Embodiment 60. An interleukin 22 (IL-22) inhibitor for use in a method of reducing skin irritation in a subject caused by application of an alternating electric field, the method comprising: delivering an interleukin 22 (IL-22) inhibitor to the subject and applying an alternating electric field to the subject at a frequency between approximately 50 kHz and approximately 10,000 kHz.

Illustrative Embodiment 61. A Janus kinase (JAK) inhibitor for use in a method of reducing skin irritation in a subject caused by application of an alternating electric field, the method comprising: delivering a Janus kinase (JAK) inhibitor to the subject and applying an alternating electric field to the subject at a frequency between approximately 50 kHz and approximately 10,000 kHz.

Illustrative Embodiment 62. The JAK inhibitor fur use of Illustrative Embodiment 61, wherein the JAK inhibitor comprises at least one of Opzelura or Tofacitinib.

Illustrative Embodiment 63. A non-receptor tyrosine-protein kinase (TYK2) inhibitor for use in a method of reducing skin irritation in a subject caused by application of an alternating electric field, the method comprising: delivering a non-receptor tyrosine-protein kinase (TYK2) inhibitor to the subject and applying an alternating electric field to the subject at a frequency between approximately 50 kHz and approximately 10,000 kHz.

Illustrative Embodiment 64. An inhibitor of epithelial differentiation for use in a method of reducing skin irritation in a subject caused by application of an alternating electric field, the method comprising: delivering an inhibitor of epithelial differentiation to the subject and applying an alternating electric field to the subject at a frequency between approximately 50 kHz and approximately 10,000 kHz.

Embodiments illustrated under any heading or in any portion of the disclosure may be combined with embodiments illustrated under the same or any other heading or other portion of the disclosure unless otherwise indicated herein or otherwise clearly contradicted by context.

Numerous modifications, alterations, and changes to the described embodiments are possible without departing from the scope of the present invention defined in the claims. It is intended that the present invention not be limited to the described embodiments but that it has the full scope defined by the language of the following claims and equivalents thereof.

What is claimed is:

1. A method for treating a subject, comprising:

delivering an interleukin 23 (IL-23) inhibitor to the subject; and applying an alternating electric field to the subject at a frequency between approximately 50 kHz and approximately 10,000 kHz.

2. The method of claim 1, wherein the subject has a tumor, and the alternating electric field is applied to the tumor of the subject.

3. The method of claim 1, wherein the IL-23 inhibitor comprises at least one of guselkumab, risankizumab, or tildrakizumab.

4. The method of claim 1, wherein the IL-23 inhibitor is formulated for topical, oral, or parenteral administration.

5. The method of claim 1, further comprising:

prior to delivering the IL-23 inhibitor to the subject, obtaining a first level of at least one of IL-23, IL-17A, or IL-22 in the subject;

obtaining a second level of at least one of IL-23, IL-17A, or IL-22 in the subject after applying the alternating electric field to the subject;

detecting an elevation of the at least one of IL-23, IL-17A, or IL-22 by comparing the first and second levels of at least one of IL-23, IL-17A, or IL-22; and delivering the IL-23 inhibitor to the subject based on the elevation of the at least one of IL-23, IL-17A, or IL-22.

6. The method of claim 5, wherein the elevation of the at least one of IL-23, IL-17A, or IL-22 is at least approximately 5%.

7. The method of claim 6, further comprising:

delivering an inhibitor to the subject who shows the elevation of at least one of IL-23, IL-17A, or IL-22 prior to delivering another alternating electric field, wherein the inhibitor comprises at least one of an IL-23 inhibitor, an IL-17A inhibitor, a RAR-related orphan receptor gamma (RORγt) inhibitor, an IL-17F inhibitor, an IL-17RA inhibitor, an IL-12Rβ1 inhibitor, an IL-23R inhibitor, an IL-22 inhibitor, a Janus kinase (JAK) inhibitor, a non-receptor tyrosine-protein kinase (TYK2) inhibitor, or a vitamin D derivative.

8. The method of claim 1, wherein at least a portion of the applying step is performed after at least a portion of the delivering step.

9. The method of claim 1, wherein at least a portion of the applying step is performed simultaneously with at least a portion of the delivering step.

10. The method of claim 1, wherein at least a portion of the applying step is performed before at least a portion of the delivering step.

11. A method of treating a subject, comprising:

delivering at least one inhibitor to the subject, the inhibitor selected from the group consisting of an interleukin 23 (IL-23) inhibitor, an interleukin 17A (IL-17A) inhibitor, a RAR-related orphan receptor gamma (RORγt) inhibitor, an interleukin 17F (IL-17F) inhibitor, an interleukin 17RA (IL17RA) inhibitor, an interleukin 12Rβ1 (IL-12Rβ1) inhibitor, an interleukin 23R (IL-23R) inhibitor, an interleukin 22 (IL-22) inhibitor, a Janus kinase (JAK) inhibitor, a non-receptor tyrosine-protein kinase (TYK2) inhibitor, and an inhibitor of epithelial differentiation; and applying an alternating electric field to the subject at a frequency between approximately 50 kHz and approximately 10,000 kHz.

12. The method of claim 11, wherein at least two inhibitors are delivered to the subject.

13. The method of claim 11, wherein at least three inhibitors are delivered to the subject.

14. The method of claim 11, wherein the IL-17A inhibitor comprises at least one of secukinumab, ixekizumab, or brodalumab.

15. The method of claim 11, wherein the RORγt inhibitor comprises at least one of JNJ-61803534 or GSK2981278.

16. A method of treating a subject, comprising:

obtaining a first level of one or more cytokines of the subject;

applying an alternating electric field to the subject at a frequency between approximately 50 kHz and approximately 10,000 kHz for a first period of time;

obtaining a second level of the one or more cytokines of the subject;

detecting an elevation of the one or more cytokines by comparing the first and second levels of the one or more cytokines; and delivering at least one inhibitor to the subject, the inhibitor selected from the group consisting of an interleukin 23 (IL-23) inhibitor, an interleukin 17A (IL-17A) inhibitor, a RAR-related orphan receptor gamma (RORγt) inhibitor, an interleukin 17F (IL-1717F) inhibitor, an interleukin 17RA (IL17RA) inhibitor, an interleukin 12Rβ1 (IL-12Rβ1) inhibitor, an interleukin 23R (IL-23R) inhibitor, an interleukin 22 (IL-22) inhibitor, a Janus kinase (JAK) inhibitor, a non-receptor tyrosine-protein kinase (TYK2) inhibitor, and an inhibitor of epithelial differentiation; and applying the alternating electric field to the subject at the frequency between approximately 50 kHz and approximately 10,000 kHz for a second period of time.

17. The method of claim 16, wherein the first level and second level of the one or more cytokines are obtained from serum samples of the subject.

18. The method of claim 16, wherein the one or more cytokines include IL-17A, interleukin 18 (IL-18), IL-22, and/or IL-23.

19. The method of claim 16, when the one or more cytokines is IL-17A, wherein an elevation of the IL-17A is at least approximately 5%.

20. The method of claim 16, wherein the inhibitor is delivered to the subject before the applying the alternating electric field to the subject or after applying the alternating electric field to the subject.

21. The method of claim 2, wherein the alternating electric field is applied using at least one pair of transducers placed on the subject and directed on a target tissue of the subject, and wherein the alternating electric field is generated using an alternating current (AC) voltage generator.

22. The method of claim 21, wherein the alternating electric field is applied using two pairs of transducers placed on the subject and directed on the target tissue of the subject.

23. The method of claim 2, wherein the frequency of the alternating electric field is at least 150 kHz.

24. The method of claim 23, wherein the frequency of the alternating electric field is between 150 kHz and 300 kHz.

25. The method of claim 2, wherein the intensity of the alternating electric field is between 1 V/cm and 10 V/cm.

* * * * *